United States Patent
Small et al.

(10) Patent No.: US 9,599,546 B2
(45) Date of Patent: Mar. 21, 2017

(54) PRESSURE MONITORING OF WHOLE BLOOD ASPIRATIONS TO DETERMINE COMPLETENESS OF WHOLE BLOOD MIXING

(75) Inventors: Nathan A. Small, Bear, DE (US); John P. Mizzer, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 57 days.

(21) Appl. No.: 13/817,412

(22) PCT Filed: Sep. 2, 2011

(86) PCT No.: PCT/US2011/050365
§ 371 (c)(1),
(2), (4) Date: Feb. 15, 2013

(87) PCT Pub. No.: WO2012/031222
PCT Pub. Date: Mar. 8, 2012

(65) Prior Publication Data
US 2013/0143257 A1 Jun. 6, 2013

Related U.S. Application Data

(60) Provisional application No. 61/379,474, filed on Sep. 2, 2010.

(51) Int. Cl.
*G01N 1/38* (2006.01)
*G01N 35/10* (2006.01)

(52) U.S. Cl.
CPC ........... *G01N 1/38* (2013.01); *G01N 35/1009* (2013.01); *G01N 2035/1025* (2013.01); *G01N 2035/1058* (2013.01)

(58) Field of Classification Search
CPC ................ G01N 35/1009; G01N 1/38; G01N 2035/1025; G01N 2035/1058
USPC ........ 435/2, 29; 73/61.41, 199–200, 170.14; 422/1, 415
See application file for complete search history.

(56) References Cited

U.S. PATENT DOCUMENTS

| | | | |
|---|---|---|---|
| 6,370,942 B1 * | 4/2002 | Dunfee | G01N 35/1016 73/1.74 |
| 2005/0014284 A1 * | 1/2005 | Jacobs | B01F 11/0071 436/180 |
| 2006/0275906 A1 * | 12/2006 | Devlin | G01N 35/00584 436/43 |
| 2009/0066339 A1 | 3/2009 | Glezer et al. | |
| 2009/0068062 A1 | 3/2009 | Jafari et al. | |
| 2009/0266149 A1 * | 10/2009 | Kaplit | G01N 35/1016 73/54.09 |
| 2010/0015690 A1 | 1/2010 | Heavner | |
| 2012/0202238 A1 * | 8/2012 | Hyde | G01N 15/042 435/29 |

* cited by examiner

*Primary Examiner* — Scott Long
*Assistant Examiner* — Nghi Nguyen

(57) ABSTRACT

Methods for use with chemical analyzers aspirate a sample portion from one location to dispense it at a second location, aspirate another sample portion at that second location and dispense it at the first location, and measure the pressure values experienced inside a probe performing the aspirations and dispenses. By comparing the pressure values (or other values indicative of the viscosity or other relevant properties of the sample), the chemical analyzer can determine if the sample is sufficiently mixed or if the sample components remain separated and the method should be repeated.

12 Claims, 9 Drawing Sheets

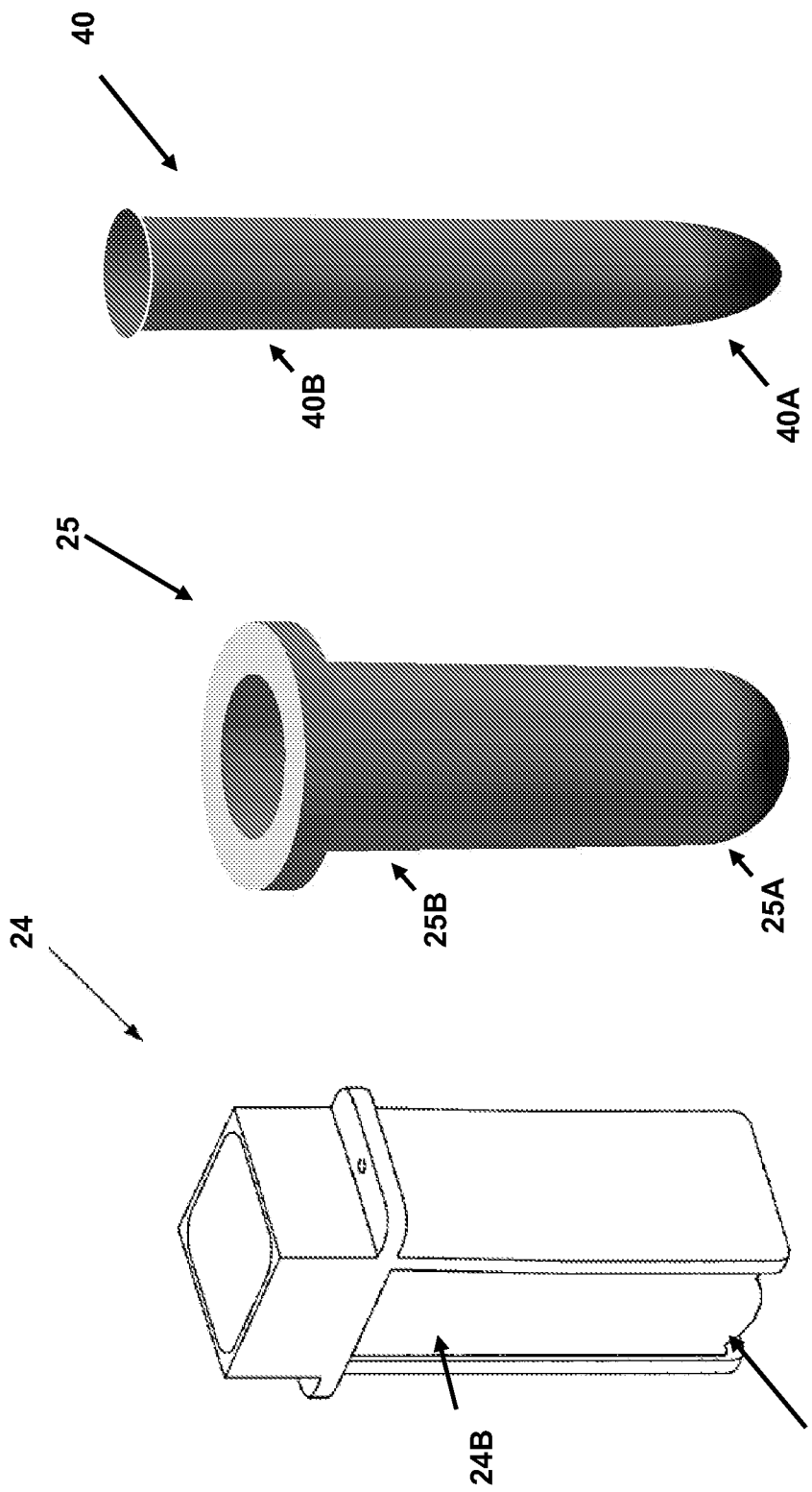

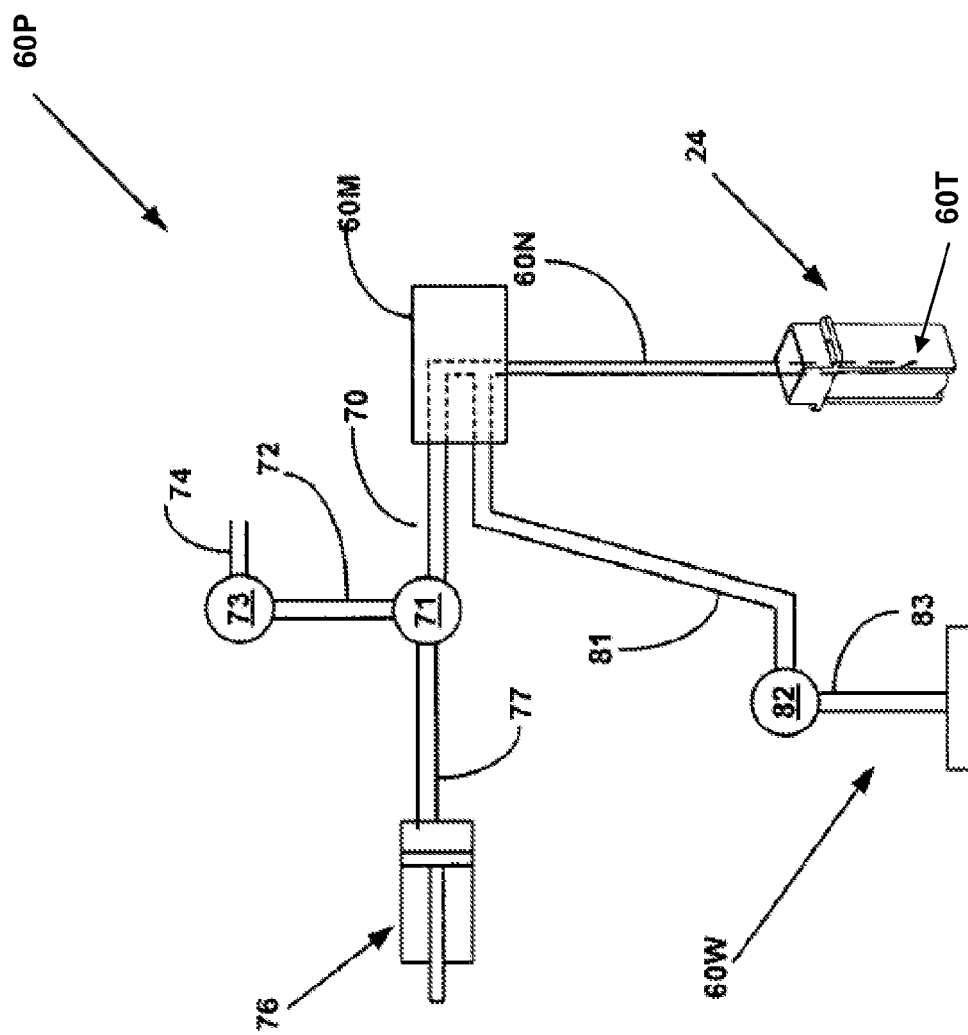

PRESSURE MONITORING OF WHOLE BLOOD ASPIRATIONS TO DETERMINE COMPLETENESS OF WHOLE BLOOD MIXING

CROSS-REFERENCE TO RELATED APPLICATIONS

This application claims the benefit of U.S. Provisional Application Ser. No. 61/379,474, filed Sep. 2, 2010, entitled "Whole Blood Re-suspension in Primary Tubes on the Dimension Vista System," which is incorporated herein by reference in its entirety.

TECHNOLOGY FIELD

The present invention relates in general to mixing and/or sensing procedures for use with diagnostic equipment and, more particularly, to a method for verifying completely mixed liquid samples, reagents, or other solutions in a container. Embodiments of the present invention are particularly well suited, but in no way limited, to providing an improved method for verifying sufficient uniformity in a blood sample using an aliquot probe or transfer device.

BACKGROUND

Various types of analytical tests related to patient diagnosis and therapy can be performed by analysis of a liquid sample taken from a patient's bodily fluids, or abscesses. These assays are typically conducted with automated clinical analyzers (ACAs) onto which tubes or vials containing patient samples have been loaded. The analyzer extracts a liquid sample from the vial and combines the sample with various reagents in special reaction cuvettes or tubes (referred to generally as reaction vessels). Usually the sample-reagent solution is incubated or otherwise processed before being analyzed. Analytical measurements are often performed using a beam of interrogating radiation interacting with the sample-reagent combination, for example, turbidimetric, fluorometric, absorption readings, or the like. The measurements allow determination of end-point or rate values from which an amount of analyte related to the health of the patient may be determined using well-known calibration techniques.

Clinical chemistry analyzers employ many different processes to identify analytes and, throughout these processes, patient liquid samples and samples in combination with various other liquids (such as reagents, diluents, or re-hydrated compositions) are frequently required to be mixed to a high degree of uniformity. The uniformity of a sample should be achieved before sample transfer and ideally maintained throughout the processing of samples, including those that naturally separate over time (e.g., whole blood). Additionally, due to increasing pressures on clinical laboratories to increase analytical sensitivity, there continues to be a need for improvements in the overall processing efficiency of clinical analyzers. In particular, sample analysis continuously needs to be more effective in terms of increasing assay throughput.

The general trend in the ACA market is to convert manual tasks to automated tasks where possible. The level of automation achieved to date varies by the sample being used. For example, urine samples may require very little manual handling, whereas whole blood samples (i.e., blood samples having cells in suspension with serum and plasma) have traditionally been handled differently, requiring an operator to shake samples to suspend blood cells before an automated diagnostic step. This manual step can lower efficiency and can be a failure point in sample processing. The additional handling needed for whole blood diagnostics of patient samples in the in-vitro diagnostics (IVD) industry also makes it difficult to converge sample diagnostics for whole blood and other samples, such as urine or blood components into a single ACA process.

Assays performed by the IVD industry are commonly referred to as "blood work" because the patient is sampled and the specimen is sent to a laboratory for testing. The main types of samples used in IVD testing are serum, plasma, urine, whole blood, and cerebral spinal fluid. Serum, plasma, and whole blood samples are all taken the same way via a needle that is connected to a blood collection tube. However, different sample tubes are commonly used for different tests which require serum, plasma, or whole blood specimens that contain different additives that are required to avoid interferences and get the desired sample consistency. Serum and plasma, rather than whole blood samples, are used in a majority of clinical chemistry tests for blood because red blood cells can cause interference in some diagnostic reactions and because the blood plasma or white blood cells contain many analytes being measured. Serum and plasma can be created by spinning blood samples in a centrifuge to separate red blood cells out in the bottom of the tube.

Whole blood samples are primarily used in assays where the analyte measured is attached to the red blood cells or where the red blood cells themselves are being sampled. On a laboratory clinical chemistry system, there are a few assays that utilize whole blood as a sample, including HbA1c (measuring the ratio of hemoglobin A1c, glycated hemoglobin in erythrocytes), ethanol, glucose, immunosuppressive drug (ISD) tests, such as cyclosporine (CSA), tacrolimus (TACR), and sirolimus (SIRO), and various hemoglobin assays. "Whole blood assays" can refer to any subset or super-set of these assays. In addition to ACAs, a laboratory can use whole blood-specific instruments, such as hematology and coagulation instruments, to perform certain whole blood assays, such as assays focused on measuring red cell count, clotting, and other macroscopic properties of whole blood. Certain assays may be incompatible with hematology and coagulation instruments or may be more suitable for ACAs. For example, immunoassays require detection technology that is most similar to serum/plasma immunoassays already available in ACAs (e.g., immunoassays generally require a reaction to take place with antibodies and a precise detection of the resulting concentration of an analyte).

Typically, ACAs are not designed to automatically handle whole blood samples. Whole blood samples are commonly collected in a Potassium EDTA salt containing tube that acts as an anti-coagulant. The sample should not clot and should be uniform prior to any transfer or analysis taking place. Even without clotting, differences in density between red blood cells and the surrounding components cause whole blood to gradually separate, with the denser red cells going to the bottom of the tube and lighter white blood cells and blood plasma staying on the top. The cells in the sample can typically be re-suspended by mixing. Mixing of the contents to re-suspend the fluid typically must to be gentle enough to avoid foaming the sample. One common mixing technique requires a laboratory technician to gently invert the tube by hand to mix it. This manual task can be somewhat automated using a simple bench top device called a sample nutator, which is typically separate from an ACA or other diagnostic device.

Some chemistry systems get around the handling of whole blood by manually pre-treating the blood with a lysing agent, typically diluting the whole blood specimen on the bench, to allow a supernatant sample to be drawn off. This sample can then be handled the same way as serum or plasma samples because these lysed components will no longer settle over time like an untreated whole blood sample. Lysing may be undesirable or impractical because it is generally only suitable for specialized low volume testing due to the amount of manual interaction with the sample and potential for human error.

A typical ACA includes mechanical mixing components for mixing solutions and samples, but these components are not designed specifically for handling whole blood samples. For example, once a sample is placed into a reaction vessel, such as a cuvette, a sample or reaction probe can be moved in a mixing pattern. Such a mixing process can introduce foaming to a viscous sample, such as whole blood. It also requires proper hardware, such as an ultrasound transducer, attached to a probe to allow rapid horizontal translation. However, mixing within the ACA can only re-suspend blood cells in the sample in the particular vessel being mixed. In the instance of whole blood, if the sample used to draw an aliquot was not fully mixed prior to aliquoting, the ratio of red blood cells to plasma and serum will not be representative of the sample, which can introduce error into subsequent assays.

Therefore, there remains a need to reliably mix samples that naturally separate over time, such as whole blood, at the time of aliquot transfer and to further verify the uniformity of the sample. To fully deliver the automation advantages of an ACA, it is desirable to provide a process that does not require a separate nutator or manual mixing step. There is a further need to address this issue without adding hardware to existing ACAs, to improve automation on existing setups.

SUMMARY

Embodiments of the present invention address and overcome one or more of the above shortcomings and drawbacks, by providing devices, systems, and methods for mixing and verifying uniformity of samples using aspirations and dispensing. This technology is particularly well-suited for, but by no means limited to, automated chemical analyzers for use with whole blood samples or other samples that have components that separate over time.

Embodiments of the present invention are directed to chemical analyzers and methods for use with chemical analyzers that aspirate a sample portion from one location to dispense it at a second location, aspirate another sample portion at that second location and dispense it at the first location, and measure the pressure values experienced inside a probe performing the aspirations and dispenses. By comparing the pressure values (or other values indicative of the viscosity or other relevant properties of the sample), the chemical analyzer can determine if the sample is sufficiently mixed or if the sample components remain separated. This also mixes the sample, allowing the steps to be repeated to mix the sample sufficiently after a number of cycles. Samples that do not meet predetermined criteria that indicate sufficient uniformity can be rejected or mixed further.

According to one embodiment of the invention, a method for mixing a sample includes aspirating a first portion of a sample to be mixed from a first level within a vessel containing the sample and dispensing it at a second level within the vessel. During at least one of the steps of aspirating or dispensing the first portion of the sample, a first set of one or more values relating to at least one property of the first portion of the sample may be measured. The method further aspirates a second portion of the sample to be mixed from approximately the second level within the vessel and dispenses it at approximately the first level within the vessel. During at least one of the steps of aspirating or dispensing the second portion of the sample, a first set of one or more values relating to at least one property of the second portion of the sample may be measured. The first set of values are compared to determine a difference of the at least one property of the first and second samples and further to determine whether the difference of the at least one property of the first and second samples meets predetermined criteria. In response to this determination, the method transfers at least a third portion of the sample to perform an assay.

According to one aspect of the invention, the sample may be whole blood. According to another aspect of the invention, the sample is a fluid having components that separate over time. According to still another aspect of the invention, one of the first level and second level is a location substantially near the top of the sample and the other of the first level and second level is a location substantially near the bottom of the sample. According to another aspect of the invention, the steps of aspirating and dispensing are repeated a predetermined number of times, such that multiple first portions of the sample are transferred from the first level to the second level and multiple second portions of the sample are transferred from the second level to the first level. According to a different aspect of the invention, the steps may be repeated until the difference of the at least one property of the first and second samples meets predetermined criteria, and the sample may be rejected, or indentified as non-conforming if the sample fails to meet the predetermined criteria after a predetermined number of times. According to yet another aspect of the invention, the predetermined criteria includes an indication that the viscosities of the first sample portion and second sample portion are substantially similar. According to one aspect of the invention, the first set and second set of one or more values comprise a first set and second set of one or more pressure values. In yet another aspect of the invention, the method further includes the steps of calculating a first pressure drop from the first set of one or more pressure values and a second pressure drop from the second set of one or more pressure values and determining whether the first and second pressure drops meet a threshold of similarity.

According to one embodiment of the invention, a method for mixing a sample includes two fluid transfer steps: one where a sample portion is aspirated from a first location in a sample and dispensed at a second location; and another where a sample portion is aspirated from substantially near the second location in a sample and dispensed substantially near the first location. Pressure values may be monitored during these fluid transfer steps to determine a pressure change during aspiration or dispensing. The pressure changes relating to the first and second fluid transfer steps can be compared to determine if the difference is within predefined criteria.

According to one embodiment of the invention, a method for mixing a whole blood sample includes aspirating a first volume of blood from a first level within a sample tube that is substantially adjacent a top surface of the sample, measuring a first plurality of pressure values during the aspiration, and dispensing the first volume of blood at a second level within the sample tube that is substantially adjacent a bottom of the sample tube. In addition, the method aspirates a volume of blood from approximately the second level, measures a second plurality of pressure values during the aspiration, and dispenses the second volume of blood at approximately the first level. This series of aspirations, measurements, and dispenses is repeated a predetermined number of times. The method calculates a plurality of slopes from the plurality of pressure values measured and calculates a plurality of differences between the plurality of slopes. The plurality of differences can then be used to determine if a viscosity of the blood at the first and second levels indicates that the blood sample is properly mixed.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 2A is a perspective view of a cuvette for use with certain embodiments;

FIG. 2B is a perspective view of another type of reaction vessel for use with certain embodiments;

FIG. 2C is a perspective view of a sample tube for use with certain embodiments;

FIG. 5 is a system view of a control mechanisms for controlling the motion and use of a probe needle for use with certain embodiments;

DETAILED DESCRIPTION OF ILLUSTRATIVE EMBODIMENTS

Figure 1:
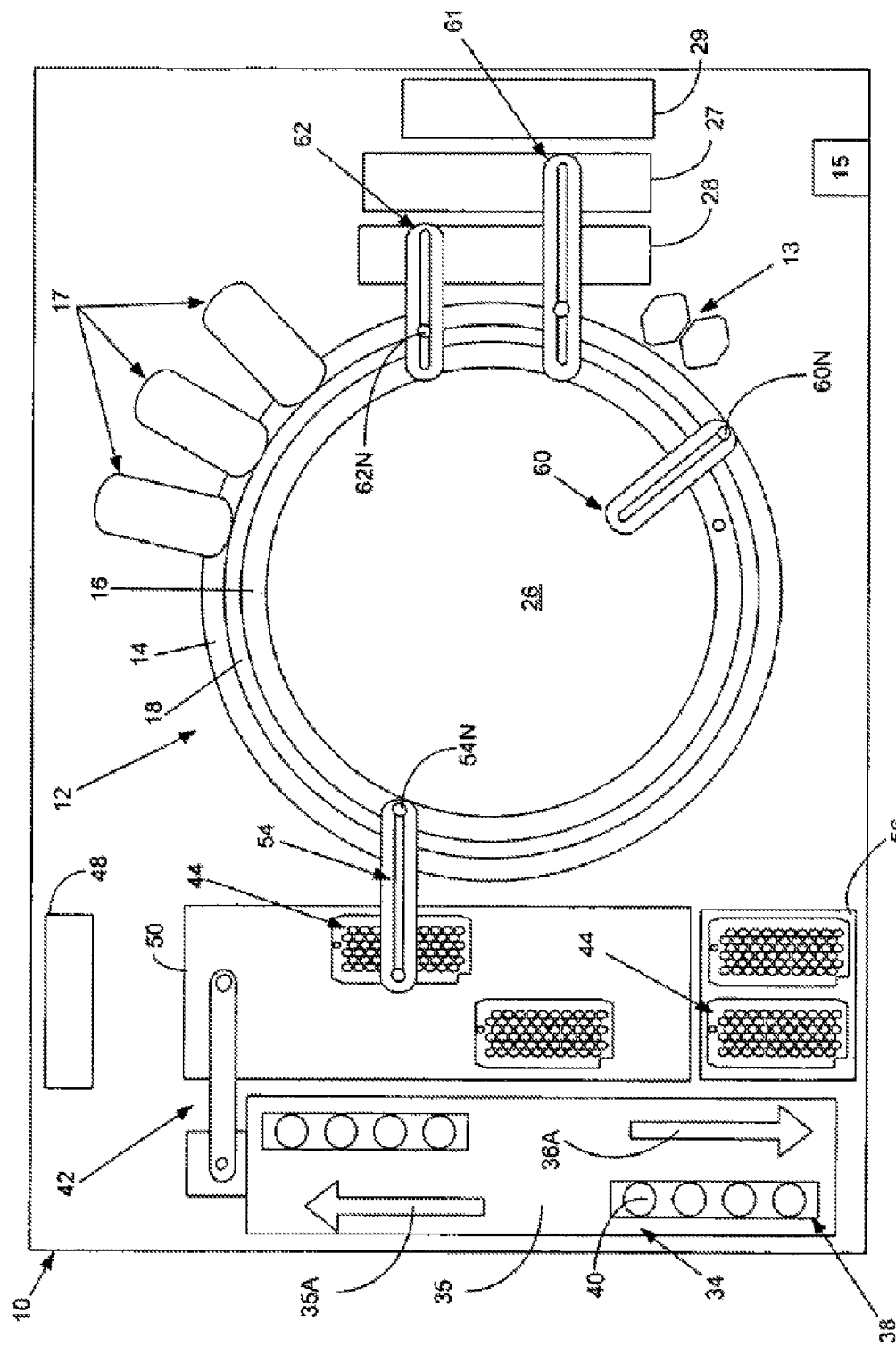
FIG. 1 is a top view of an exemplary chemical analyzer in which embodiments of the vertical alignment and mixing method and apparatus may be employed.

The above problems in the prior art have motivated the discovery of improved apparatus and methods for reliably and/or automatically creating and/or verifying uniformity of sample components within a fluid sample. By observing viscous properties of the sample during aspiration or dispensing of a portion at different levels within the sample, the relative mixture of fluid components can be compared to verify uniformity. In some embodiments, a sample can be aspirated and dispensed (i.e., "sip and spit" mixing) at different heights until the relative observed pressures are substantially similar. The observation (or measurement) of pressures during aspiration/dispensing can be used to verify that a pre-determined mix routine was effective, to determine when to stop a mixing routine, to determine an expected length of a mixing routine needed to further effectively mix a sample, or to reject a sample as non-conforming in instances where a sample is not observed to be fully mixed as expected.

Embodiments can be suitable for use with whole blood samples, or other samples in which components separate over time or in which components have different viscosities, where it is desirable to have the components uniformly mixed. For simplicity of description, these samples can be referred to as colloids. The term sample can be used broadly to include reagents, fluids, and the like. These methods are particularly suitable for unstable colloids, such as blood, which can be mixed to a homogenous state, but will become heterogeneous over time due to some process, such as density driven separation (e.g., part of the mixture settles out). These methods may also be suitable for inadvertent colloids/heterogeneous mixtures (e.g., where a sample is not expected to be colloidal or to have particulates, or where an unexpected foreign substance may be in the sample). For simplicity, the states can be referred to as homogenous (e.g., mixed or uniform) and heterogeneous, as they do not form a single uniform solution.

In the instance of whole blood, the colloidal properties are often exploited to separate plasma, serum, and hematocytes, such as by spinning a sample in a centrifuge to settle the different components into layers. In this case, the spinning works because components have different densities, and the heavier components settle out to the bottom (e.g., the hematacytes will settle further down than the serum, etc.) However, these colloidal properties also cause gradual settling of samples when they sit for periods of time.

The different densities of the components cause the different layers within a heterogeneous/settled sample to have different properties, such as densities and/or viscosities. The differences in density, viscosity, or other properties of the various layers can be observed by sampling the fluid at different heights and comparing the properties. For example, density or viscosity can be observed by aspirating or dispensing a portion of the sample at different heights in a sample vessel and observing the back pressure created, the flow rate, optical properties, or any other properties that correlate to the different properties of the different layers that settle out. For example, sampling the bottom portion of a sample that has settled can result in greater back pressure when aspirating or dispensing, a slower flow rate during the aspiration/dispensing, and/or can reveal a sample portion that is darker optically. Other properties that may be used might include electrical properties, precise weight of a volume of sample extracted, optical properties, turbidity properties, or the like.

It will be appreciated that values relating to differences in properties of the sample at two locations within the sample can reveal differences in other properties of the sample. For example, pressure values can reveal the relative differences in viscosity between two portions of a sample (such as a portion at the bottom and a portion at the top). Mass values, such as the mass of the probe before and after an aspiration can reveal differences in the density of the sample portions. Reflection, refraction, color, or optical scattering values can reveal optical differences in portions of the sample indicating heterogeneity in the sample. Electrical values, such as voltage or capacitance, can reveal differences in ions or electrical properties of two portions of the sample, which can also reveal a heterogeneous colloidal sample.

Figure 2:
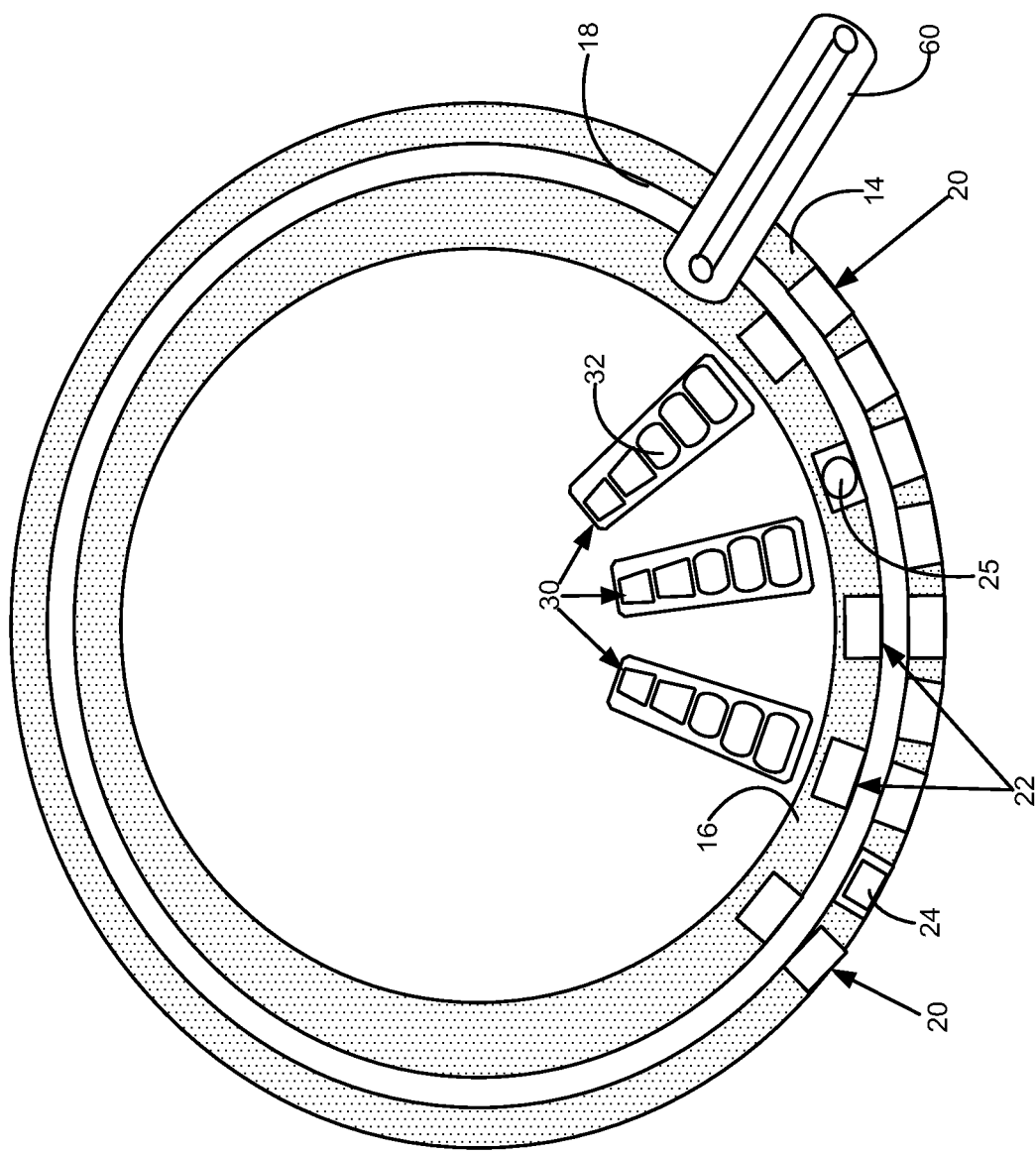
FIG. 2 is a top view of a portion of a carousel for transporting reaction vessels and cuvettes for use with certain embodiments.

FIG. 1, taken with FIG. 2, shows schematically the elements of an automated chemical analyzer (ACA) 10 in which the present invention may be advantageously practiced. This may include, for instance, the chemical analyzer described in U.S. Pat. No. 7,258,480, which is incorporated herein by reference. As shown in FIGS. 1 and 2, analyzer 10 comprises a reaction carousel 12 supporting an outer carousel 14 having cuvette ports 20 formed therein and an inner carousel 16 having vessel ports 22 formed therein, the outer carousel 14 and inner carousel 16 being separated by an open groove 18.

Reaction carousel 12 is rotatable using stepwise movements in a constant direction, the stepwise movements being separated by a dwell time during which reaction carousel 12 remains stationary and computer controlled assay operational devices 13, such as sensors, reagent add stations, mixing stations, and the like, operate as needed on an assay mixture contained within a cuvette 24. Reaction carousel 12 may be operated in a random access or sequential manner, such that the number of rotation steps that a sample undergoes between stations can be fixed or vary depending on operation. The dwell time between cycles can be generally constant (or variable), but the amount of time a sample sits before a test is conducted can be variable. Accordingly, at least in some instances of operation, a sample in a cuvette can wait long enough between two stations to begin settling out if the sample is colloidal.

Analyzer 10 is controlled by software executed by a computer 15 based on computer programs written in a machine language like that used on the Dimension® clinical chemistry analyzer sold by Siemens Healthcare Diagnostics Inc. of Deerfield, Ill., and widely used by those skilled in the art of computer-based electromechanical control programming. Computer 15 also executes application software programs, such as the Dimension Vista® system software for performing assays conducted by various analyzing means 17 (e.g., detection units) within analyzer 10. Analyzing means can include, for instance, one or more photometers, turbidimeters, nephelometers, electrodes, electromagnets, and/or LOCI® readers for interpreting the results of reactions within the reaction vessels or cuvettes.

As seen in FIG. 1, a bi-directional incoming and outgoing sample fluid tube transport system 34 comprises a mechanism for transporting sample fluid tube racks 38 containing open sample fluid containers such as sample fluid tubes 40 from a rack input load position at a first end of the input lane 35 to the second end of input lane 35 as indicated by open arrow 35A. Fluid tubes 40 are typically much larger than the reaction vessels and cuvettes used in the reaction carousel, and can typically provide a plurality of aliquot samples to allow multiple parallel assays. Liquid specimens contained in sample tubes 40 can be identified by reading bar coded indicia placed thereon using a conventional bar code reader to determine, among other items, a patient's identity, tests to be performed, the type of sample, if a sample aliquot is to be retained within analyzer 10, and, if so, for what period of time. It is also common practice to place bar coded indicia on sample tube racks 38 and employ a large number of bar code readers installed throughout analyzer 10 to ascertain, control, and track the location of sample tubes 40 and sample tube racks 38. The barcode can also be used to determine if the sample is a colloidal sample, such as whole blood, such that the system knows that homogeneity must be verified or maintained during processing.

A conventional liquid sampling probe 42 is located proximate the second end of the input lane 35 and is operable to aspirate aliquot portions of sample fluid from sample fluid tubes 40 and to dispense an aliquot portion of the sample fluid into one or more of a plurality of vessels in aliquot vessel array 44. This provides a quantity of sample fluid to facilitate assays and to provide for a sample fluid aliquot to be retained by analyzer 10 within an environmental chamber 48. For non-emulsified samples, such as whole blood, it is generally desirable that the sample be mixed uniformly before transferring to aliquot arrays 44 to ensure consistent samples within the array. After sample fluid is aspirated from all sample fluid tubes 40 on a rack 38 and dispensed into aliquot vessels in array 44 and maintained in an aliquot vessel array storage and transport system 50, rack 38 may be moved, as indicated by open arrow 36A, to a front area of analyzer 10 accessible to an operator so that racks 38 may be unloaded from analyzer 10.

Sample aspiration probe 54 is controlled by computer 15 and is adapted to aspirate a controlled amount of sample from individual aliquot vessels in array 44 positioned at a sampling location within a track (not shown) and is then shuttled to a dispensing location where an appropriate amount of aspirated sample is dispensed into one or more cuvettes 24 for testing by analyzer 10 for one or more analytes. After sample has been dispensed into reaction cuvettes 24, conventional transfer means move aliquot vessel arrays 44, as required, within aliquot vessel array storage and dispensing module 56 between aliquot vessel array transport system 50, environmental chamber 48, and a disposal area (not shown).

Cuvette ports 20 are adapted to receive a plurality of reaction cuvettes 24, as seen in FIG. 2A, that contain various reagents and sample liquids for conventional clinical and immunoassay assays. Vessel ports 22 can be adapted to receive a plurality of reaction vessels 25, as shown in FIG. 2B, that contain specialized reagents for ultra-high sensitivity luminescent immunoassays. Similarly, an exemplary sample fluid tube 40 is shown in FIG. 2C. Sample fluid tubes 40, cuvettes 24, and reaction vessels 25 can include bottom portions 40A, 24A, and 25A, and top portions 40B, 24B, and 25B, respectively. While sample fluid tubes, cuvettes, and reaction vessels can have differing shapes, as used herein, the methods for mixing can be applied to the contents of fluid tubes 40, reaction vessels 25, cuvettes 24, or any other suitable vessel for holding a sample. The terms reaction vessels and cuvettes should be considered broadly and interchangeably; each of vessels 24, 25, and 40 can be referred to generally as vessels. Vessels can include, for instance, cuvettes, vials, tubes, or other suitable containers for holding samples of mixing reagents and solutions. In some embodiments the sample tube 40 is a 13×75 mm sample tube or shorter (e.g., 13×65 mm). Some vessels may have a maximum fill volume of 4 mL or less.

Temperature-controlled storage areas or servers 26, 27, and 28, contain an inventory of multi-compartment elongate reagent cartridges 30 loaded into the system via input tray 29, such as those described in U.S. Pat. No. 6,943,030 assigned to the assignee of the present invention, containing reagents in wells 32 that perform a number of different assays, and incorporated herein by reference. Reagents may be moved and aligned within analyzer 10 by any conventional means, including those described in PCT/US2010/042600, also assigned to the assignee of the present invention, and incorporated herein by reference. Computer 15 can control and track the motion and placement of the reagent cartridges 30. Reagents from server 26, 27, and 28 can be handled by one or more reagent probe arms, 60, 61, and 62.

Figure 3:
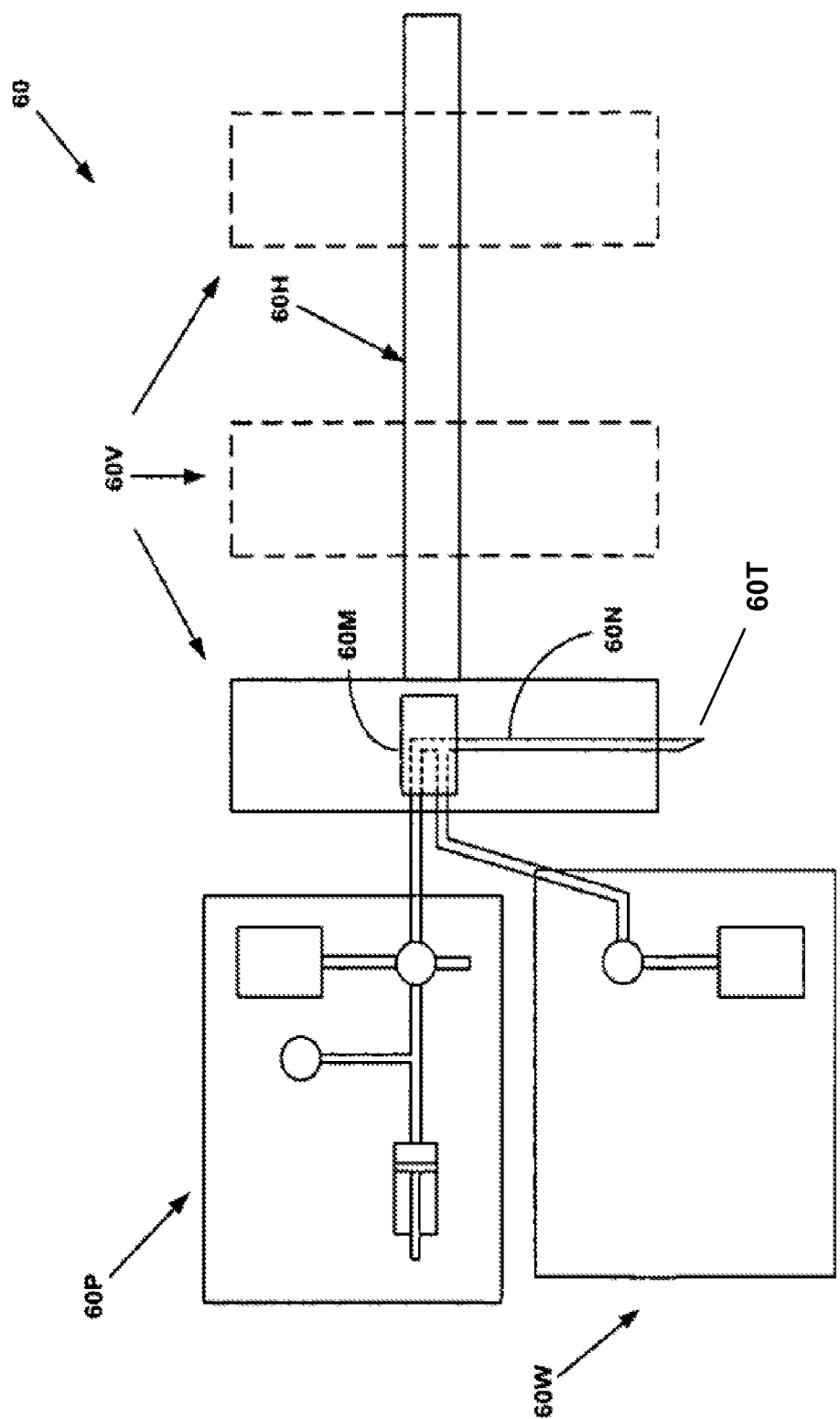
FIG. 3 is a system view of a control mechanisms for controlling the motion and use of a probe needle for use with certain embodiments.

Reagent aspiration probe 60 is an exemplary probe that can be useful in performing the present invention, as may be seen in FIG. 3. Other probes, such as 42, 54, 62, and 61 may also be useful in performing the present invention (e.g., sampling probe needles 54N and 62N are shown in FIG. 1). These probes may not have all the components discussed in the context of probe 60 or may include additional components, as probe 60 is merely intended to be illustrative (e.g., sampling probe needle 60N is shown in FIG. 1). It will be appreciated, that the methods discussed herein can be used by more than one probe including, for example, sampling probe 42, which can be used to ensure that the sample in vessel 40 is homogenous before segregating into aliquot plates 44, along with similar usage by sample aspiration probe 54 to ensure that homogenous samples are dispensed into vessels 24 or 25 in the carousel 12.

As shown in FIG. 3, an exemplary probe can comprise a horizontal drive component 60H, a vertical drive component 60V, a wash module component 60W, a pump module component 60P, an aspiration and dispensing probe needle 60N, which may include a tapered needle tip 60T designed to puncture the covering of reagent cartridge 30, and a wash manifold component 60M having the primary functions described in Table 1 below. Components of the wash module component 60W and pump module component 60P identified in FIG. 3 will be described below. Horizontal drive component 60H and vertical drive component 60V are typically computer controlled stepper motors or linear actuators and are controlled by computer 15 for providing precisely controlled movements of the horizontal drive component 60H and vertical drive component 60V.

TABLE 1

| Module | Primary Functions |
| --- | --- |
| Horizontal Drive 60H | Position the vertical drive 60V over reagent cartridges 30 containing reagent liquids and over cuvettes 24 carried in ports 20. |
| Vertical Drive 60V | Drive probe 60N through the covering of a reagent cartridge 30 for aspiration of reagents and place the tip 60T into cuvettes 24 for dispensing of reagents and mixing. |
| Wash Module 60W | Remove contamination from probe tip 60T with liquid cleansing solutions. |
| Wash Manifold 60M | Connect probe tip 60T to pump module 60P. |
| Pump Module 60P | Pump reagent liquids and sample fluids and create positive or negative pressure to aspirate or dispense fluid samples or reagents. |
| Probe Needle 60N | Aspirate and dispense reagent or sample liquids and sample fluids. |

Figure 4:
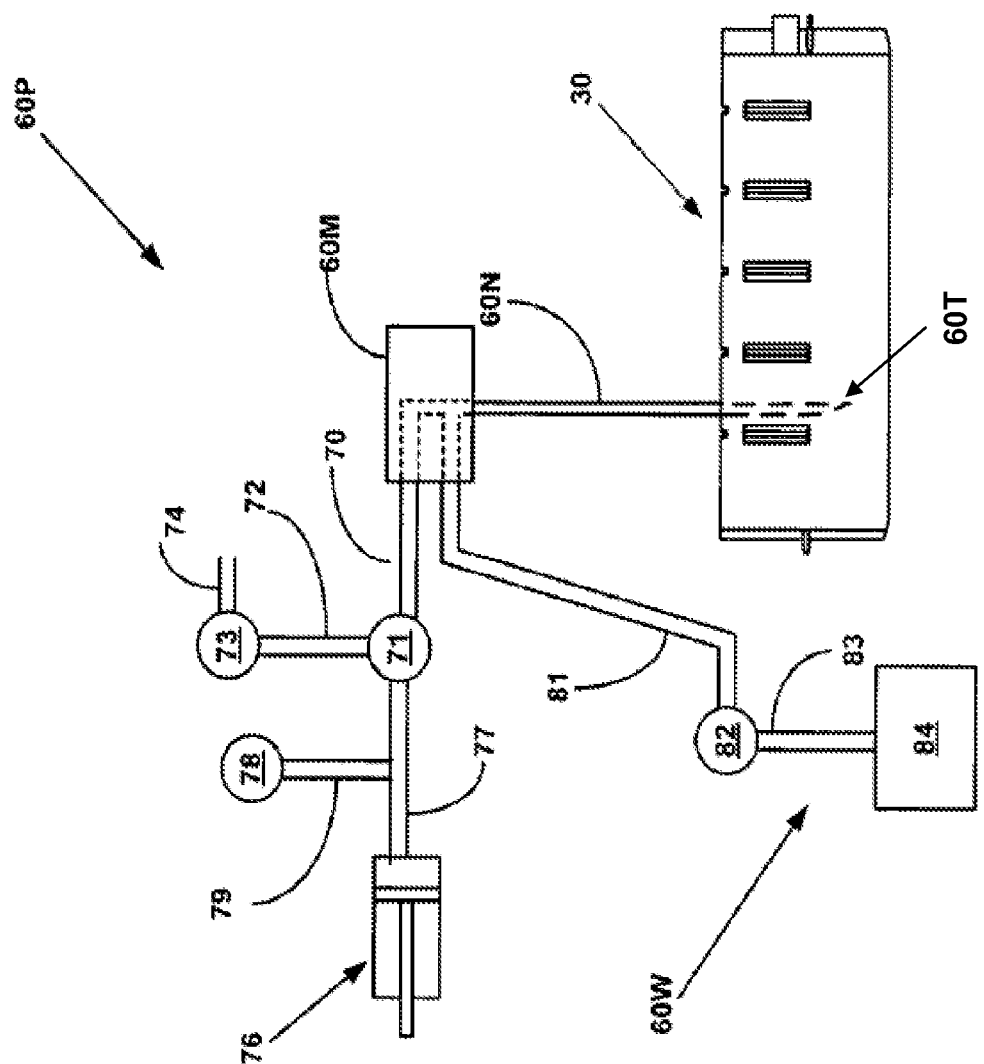
FIG. 4 is a system view of a control mechanisms for controlling the motion and use of a probe needle for use with certain embodiments.

FIGS. 4 and 5 show pump module 60P connected to a conventional, hollow, liquid-carrying probe 60N having conventionally defined interior and exterior surfaces and supported by wash manifold 60M, the wash manifold 60M being connected by a hollow air tube 70 to a three-way valve 71. Probe needle 60N may be connected to wash manifold 60M using any of several screw-like connectors, clips, or, alternately, permanently affixed or welded thereto. Valve 71 is operable to optionally connect air tube 70 to (1) air tube 72 to a vent valve 73 connected to an atmospheric vent tube 74, or (2) a piston-type syringe pump 76 by a hollow air tube 77. An air pressure measuring transducer 78 is connected to air tube 77 between pump 76 and valve 71 by a hollow air tube 79. In some embodiments, pressure transducer 78 generates a digitally encoded pressure value that can be sampled hundreds of times per second, allowing real-time analysis of the state of the aspirate in the probe.

FIG. 4 also illustrates probe tip 60T and needle 60N having punctured the covering of a reagent carrier 30 and positioned within a reagent liquid contained therein. FIG. 5 illustrates a probe tip 60T in a sample vessel 24. Level sensing means (for example, using well known capacitive signals) may be advantageously employed in order to ensure that probe needle 60N is in fluid communication with the liquid. Piston 76 is activated and the distance it is moved is controlled by computer 15 so that a controlled volume of reagent liquid is withdrawn or aspirated into probe needle 60N. During this process, valve 71 is closed to vent tube 72, but is open to air tube 77 and air tube 70. Valve 71 is operable to optionally connect air tube 70 to an optional vent valve 73 connected to an atmospheric vent tube 74. FIGS. 4 and 5 also show an optional wash manifold 60W as comprising a flush valve 82 connected to wash manifold 60W by a hollow liquid carrying tube 81. Flush valve 82 is operable to connect liquid carrying tube 81 to a pressurized rinse water source 84, which may contain water or any other suitable cleaner, by a hollow liquid tube 83.

During normal operation, a known quantity of a sample can be aspirated from one vessel, moved, and dispensed into another vessel that is accessible to the probe. However, instead of just taking a single aspiration and dispensing it into another vessel, the probe can be used to mix the sample by conducting multiple aspirations and dispenses of some portion of the sample. This is nicknamed "sip-and-spit" mixing and can be employed even where a probe lacks other mixing apparatus, such as ultrasonic drives that allow the tip to be moved rapidly in a mixing pattern.

Piston 76 can be used to aspirate or dispense a sample portion from any vessel the probe tip is placed in. For example, probe 42 (FIG. 1) can aspirate and dispense sample in tubes 40 and in the vessels of aliquot trays 44. This can allow transfer of sample from tubes 40 to aliquot trays 44, and can also allow successive aspiration and dispensing in one of these vessels to mix the sample by sip-and-spit mixing. This process can be used to homogenize a colloidal sample that has been sitting and may have settled out. This type of mixing can be used by any probe that is used to transfer a liquid by using the mechanisms ordinarily used for aspiration and dispensing. It can also be used with probes that lack horizontal drive mechanisms suitable for mixing in a stirring pattern.

The aspiration/dispense mechanism, such as piston 76, can also be used to determine whether a colloid sample is sufficiently homogenous. Pressure transducer 78 can be used to measure the pressure generated in the probe as sample is aspirated/dispensed. For example, as piston 76 is moved by a known distance (which can be determined by distance encoding or the like), the pressure measured by the pressure transducer 78 can be used to glean physical properties of the fluid in the probe. For example, a more viscous sample can create a greater pressure drop; denser samples will generally create more pressure drop. Accordingly, the pressure transducer 78 can be used to monitor properties of the fluid sample in real-time fashion.

By monitoring the physical properties at different levels in a sample vessel during a sip-and-spit process, any differences at different locations or heights can be determined. Differences can be used to determine that a sample is heterogeneous. For example, more viscosity or density at a lower level in the vessel can indicate that a colloidal sample has settled out while sitting. Conversely, substantial similarity between the physical properties at different levels of the sample can indicate that the sample components are distributed homogenously. Furthermore, because the properties can be monitored during a sip-and-spit mixing process, a colloidal sample can become more homogenous during the monitoring process. Multiple cycles of aspiration and dispensing can improve the measured homogeneity.

In some embodiments, a volume/number of aspirations and dispenses during a sip-and-spit monitoring period can be sufficient to mix a fully settled/heterogeneous colloidal sample to a sufficiently homogenous state to utilize the sample in the next step of an assay in the analyzer 10. Furthermore, if, after a period of one or more sip-and-spit mixing cycles, the sample does not reach a sufficiently homogenous state, the sample can be rejected as an anomalous or aberrant sample. In this manner, each sample in a vessel can be confirmed as homogenous before moving to the next step in the ACA, or at a particular step in the process.

Figure 7:
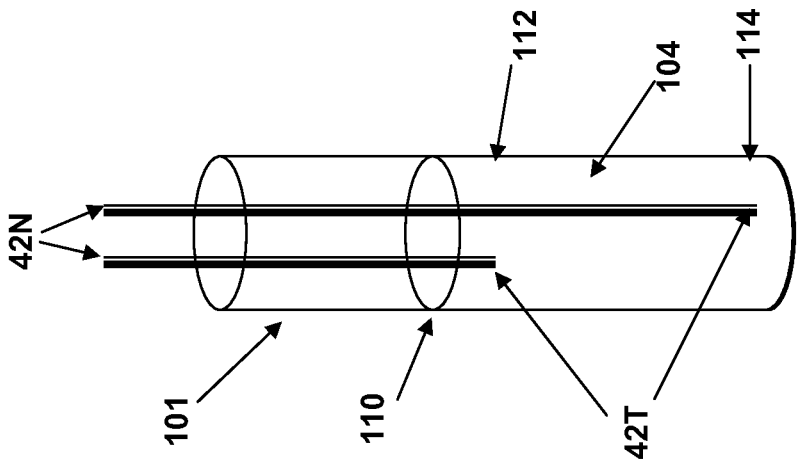
FIG. 7 is a perspective view of a vessel illustrating aspiration locations for use with some embodiments.
Figure 6:
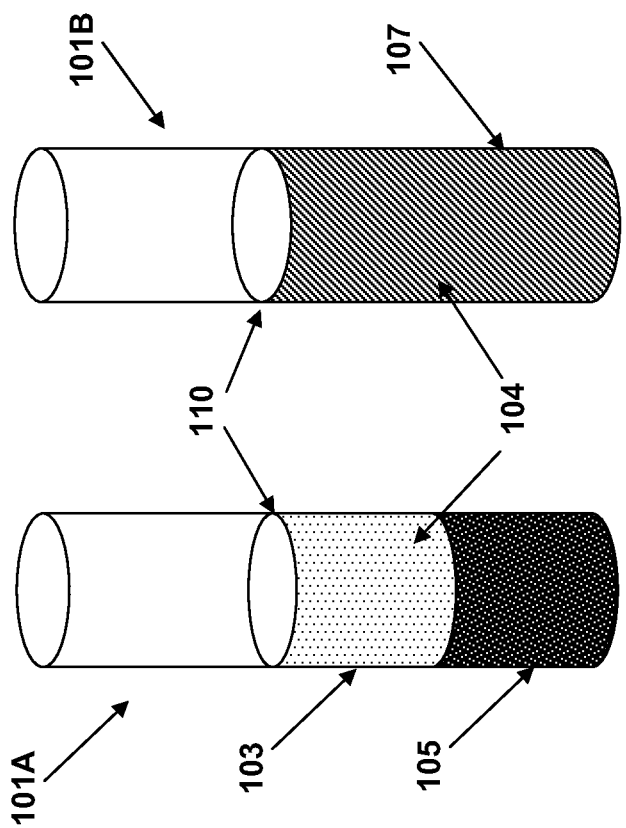
FIG. 6 is a perspective view of vessels containing mixed and unmixed samples.
Figure 8:
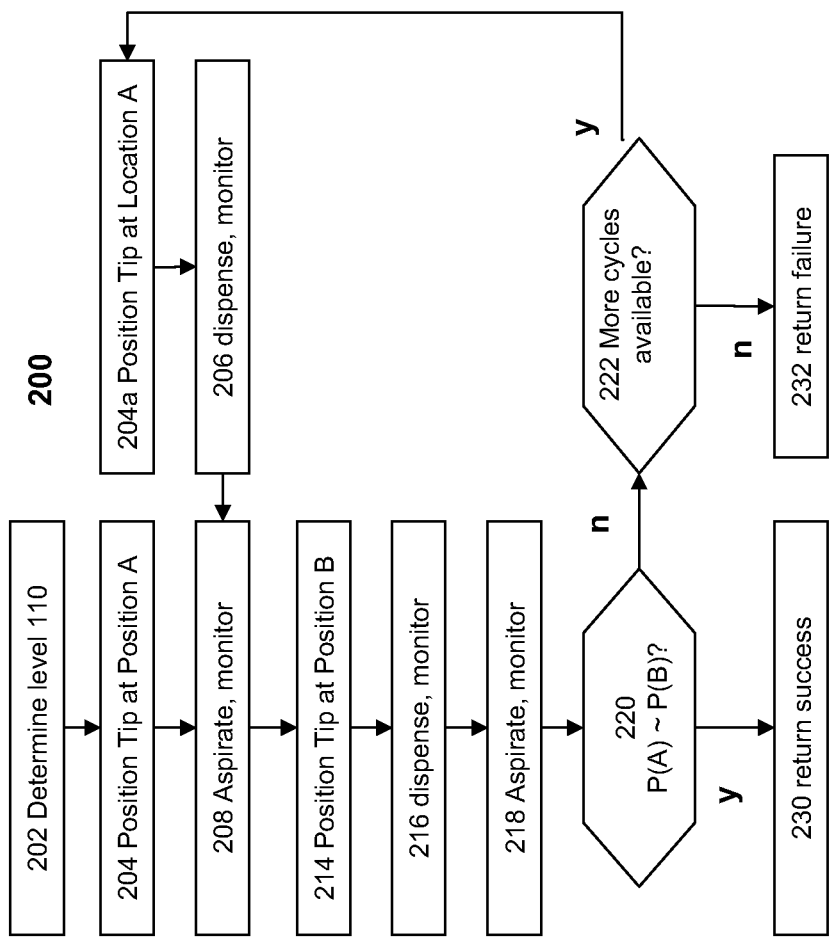
FIG. 8 is a flow diagram of the operation of a mixing procedure for use with certain embodiments.

An exemplary operation of a mixing and testing operation can be seen in FIGS. 6-8. FIG. 6 shows two extreme states of vessel 101. Vessel 101A shows a heterogeneous state, where the sample 104 has settled into components 105 and 103. For instance, lighter components 103 could contain plasma and serum for whole blood, while heavier components 105 could include hematocytes. Vessel 101B shows a homogenous state, where the sample 104 forms a substantially uniformly mixed liquid 107. In either state, the sample 104 includes a top surface 110. A probe tip, such as 42T, must be below the position of surface 110 to aspirate sample. Probe tip 42T is the tip of probe needle 40N, which may be substantially similar to probe needle 60N and tip 60T, described with respect to probe 60.

FIG. 7 shows exemplary positions of probe tip 42T for use with the mixing and testing methods herein. A first level 112 is substantially near (or adjacent to) the surface 110 of the sample 104. Aspirating or dispensing near level 112 allows the probe tip 42T to interact with the components (such as serum and plasma, where the sample 104 is whole blood) that settle out to the top of the sample, to the extent the sample 104 is heterogeneous. Level 112 can be chosen such that a subsample taken of sample 104 does not deplete the volume such that surface 110 drops undesirably below level 112. A second level 114 is substantially near (or adjacent to) the bottom of the sample 104. Aspirating or dispensing near level 114 allows the probe tip 42T to interact with the components (such hematocytes, including red blood cells) that settle out to the bottom of the sample, to the extent the sample 104 is heterogeneous. In some embodiments, level 112 corresponds with a position around top portions 24B, 25B, or 40B of these respective vessel types. In some embodiments, level 114 corresponds with a position around bottom portions 24A, 25A, or 40A of these respective vessel types. Levels 112 and 114 can be predetermined and fixed heights, or heights determined based an identified surface 110 and the bottom of the vessel. In some embodiments, levels 112 and 114 are a fixed distance from an estimate of the location of surface 110 and/or the bottom of the vessel.

The position of the surface 110 can be determined by measuring the capacitance of the probe needle 42N. Typically, the height of fluid in the tube is not a major concern because a typical ACA is designed to sample as close to the top of the fluid as practical for non-whole blood specimens. To accomplish this, capacitive level sense is used to detect the liquid level and the probe goes just far enough under this level to aspirate some desired volume (e.g., 50-325 uL). A capacitive level sense can detect a change in capacitance of a probe needle to indicate contact with a fluid. This capacitive level sense can be used to determine any level in the fluid relative to the surface, as the change in capacitance correlates to the change in depth of the probe in the fluid. The capacitive level sense can be used to determine the location of the surface 110 of the liquid and this level can be considered when choosing aspiration heights in accordance with the embodiments described throughout. In some embodiments, optical means such as a camera can be used to determine the level of the surface 110 of the sample.

Some types of serum and plasma tubes may contain gel that separates the serum/plasma from the red cells when centrifuged. Aspirating this gel is highly undesirable as it gets stuck on the inside of the probe and does not come off easily. Eventually, the probe can become clogged and need replacement. Furthermore, for a highly settled sample, there may be large concentrations of cells needing to be broken up that are located at the bottom of the tube. By placing levels 112 and 114 near the top and bottom of the fluid, respectively, differences in the properties of the sample at the location of the probe tip 42T can be used to indicate a heterogeneous state, such as 101A. If the properties of the fluid sample 104 at locations 112 and 114 are substantially similar, it could indicate a homogeneous state, such as 101B.

FIG. 8 illustrates an exemplary method 200 for determining if a sample, such as colloidal sample 104, is suitably homogenized to enable completion of the next step in an assay. For purposes of illustration, the sample will be discussed as whole blood, but other colloidal samples may be appropriate. Method 200 begins at step 202. Prior to mixing for whole blood re-suspension, at step 202, the ACA determines that the sample is present and not clogged, as well as the level 110 of the sample fluid. This can be done in any conventional manner, such as optically or capacitive sense on the probe needle 42N to determine the approximate height of surface 110. At step 202, the ACA can also determine the location of heights 114 and 112. For example, location 112 can be predetermined as a fixed distance, such as 7 mm from the surface 110. Similarly, because the dimensions of the vessel 101 should be known, the ACA can have a prior knowledge of the location of the bottom of the vessel. Level 114 can be predetermined to be a set distance from the bottom of the vessel.

In some embodiments, the level sense capability can indicate the absence of sufficient sample. For instance, if the ACA it fails to detect fluid above a specified height, such as some predetermined height in upper portion 24B, 25B, or 40B, the sample is flagged as insufficient sample and the mixing sequence can be halted to prevent further aspirating air and risking any malfunctions.

At step 204, the probe tip 42T is moved to a predetermined position A. Position A may be level 112 or 114, for instance. For sake of illustration, the probe will be moved to level 112 to begin at a point near the surface 110, but level 114 may also be suitable.

Once the probe tip is in position, at step 208, the probe aspirates some portion of the sample, such as 250 uL. This amount should be sufficiently small that the height of the surface 110 does not fall below the tip 42T. During this aspiration, the pressure in the probe can be monitored via transducer 78. As discussed herein, this can be used to estimate physical properties of the fluid at location A.

At step 214, the probe tip 42T is moved to a predetermined position B. Position B may be level 114 or 112, for instance. For sake of illustration, the probe will be moved to level 114 to take an additional sample point where position A is level 112. It should be appreciated that while this method is discussed with two sample positions, some embodiments can utilize any number of sample positions to mix and/or evaluate homogeneity. In some embodiments, aspirations are taken at the same place on the top and at the bottom throughout the mixing cycle and taken with the same volume and speed.

Level 114 can be chosen to be close to the bottom of the vessel so that the dispensing action of step 216 can break up any densely packed cells. These dispense actions also help to loosen the surface tension of red cells stuck along the walls of the container. For this reason, in some embodiments, it may be desirable to move the probe tip 42T laterally between successive cycles of method 200 to limit the amount of material that may stick to the walls.

Once the probe tip is in position, at step 216, the probe dispenses the sample portion aspirated from position A. Generally, the entire amount previously aspirated will be dispensed, but a subset could also be used, if desired. The dispensing action causes a mixing effect at position B due to turbulent flow and also moves sample components from position A to position B via direct transfer by the probe. As can be appreciated, multiple cycles of this type of aspirate-move-dispense technique can be used to counteract settling out, as components are actively conveyed in a vertical fashion. As with aspiration, the pressure during the dispensing can be measured by transducer 78.

At step 218, the probe aspirates some portion of the sample, such as 250 uL. This draws fluid from position B, which can then be used to dispense at position A, as so on. This effectuates volume transfer between positions A and B in addition to turbulent mixing during dispensing steps; during this aspiration, the pressure in the probe can be monitored via transducer 78. As discussed herein, this can be used to estimate physical properties of the fluid at location B. It should be noted that in some embodiments, there may be deviation between the location of the dispense at step 216 and the aspiration 218, as both can occur approximately at position B, perhaps deviating by a few mm.

The pressure drop that occurs inside the probe when fluid is aspirated is proportional to the viscosity of the sample aspirated. The pressure transducer 78 is used to generate a total pressure drop from prior to the aspiration to just after the aspiration. In embodiments where the pressure transducer measures pressure many times per second and per aspiration, pressure data points can be averaged and filtered for noise. In some embodiments, the pressure drop prior to the aspiration and just after the aspiration can be determined by observing the pressure during the aspiration and determining a slope of the pressure as the piston controlling the aspiration moves. This slope can be determined from any number of the pressure values observed by the transducer. In some embodiments, this slope can be stored and displayed graphically to the operator. The pressure drop observed over the range of the piston during aspiration or dispensing can be referred to as a slope, a differential, or a drop.

When a freshly mixed whole blood sample is aspirated, the viscosity of the sample at the top and the bottom should be the same except for an offset due to the fluid pressure differential between the top and the bottom. When a significantly settled sample is aspirated at the top and the bottom, the viscosity will be very different. Over the course of the mixing sequence, the viscosity at the top and the bottom should equilibrate, which is an indication that the mixing sequence is successful.

At step 220, the pressures observed during aspiration and/or dispensing at positions A and B are compared. This can generate a differential value or ratio of pressure values, which will be referred to as the comparative value, delta. In some embodiments, delta can be defined as:

Delta=$(Pmax-Pmin)_{bottom}-(Pmax-Pmin)_{top}$, or more generically: Delta=pressure slope (bottom)−pressure slope (top).

This delta value can be utilized in a number of ways. For example, delta can be compared to predetermined criteria that indicate a level of acceptable homogeneity. The predetermined criteria can include, for instance, a threshold that indicates that the viscosities of the sample at positions A and B are substantially similar. That is, if delta is less than a predetermined amount of pascals, it can indicate that the sample is substantially mixed. In some embodiments, the threshold may be expressed as a percentage of the pressure slope observed at position A or B. In some embodiments, delta is expressed as a ratio of the pressure slopes at positions A and B. That ratio can also be compared to predetermined criteria to determine if the sample is suitably mixed.

It should be appreciated that that pressures observed at A and B, and accordingly delta, will tend to converge over successive cycles of method 200 for a healthy sample. Thus, for a healthy sample, there should be some number of sip-and-spit cycles that will result in a delta that meets a threshold condition for acceptable homogeneity.

In some embodiments, the delta value can be used to estimate the number of additional cycles of method 200 that are needed to reach a delta that indicates an acceptable level of homogeneity. This can be helpful in determining if homogeneity can be reached within a single period of operation in the system, such as a mixing cycle or the dwell time of the carousel, whether an additional period will be sufficient, or whether the sample is anomalous and should be rejected as too difficult to homogenize or as exceeding acceptable levels of heterogeneity. Similarly, deltas observed during successive cycles of method 200 can be used to monitor progress in making the sample 104 homogenous.

At step 220, if the delta of the relative pressures meets requirements, the process proceeds to step 230, and the cycle returns success. The sample is ready for aspiration and transfer, or the next steps in the assay. If the delta value does not meet requirements, the method continues to step 222, where the ACA determines if more time is still available for an additional sip-and-spit cycle. For example, if the period of the system is running out, there may not be time available for the sample to continue homogenizing a sample.

It will be appreciated that step 220 can be delayed for a fixed number of cycles of routine 200. For example, where the period of the system is fixed, a fixed number of cycles (such as 8) of routine 200 may be available for mixing. Intermediate cycles can be performed with or without comparing pressure values. At the completion of the cycles, the pressure values can be compared to determine whether to accept or reject the sample.

In some embodiments, the sample will be rejected at step 232 if no more time is available. In some embodiments, at step 232, other modules can be alerted of the need for an additional period. The ACA can schedule the sample to be mixed again during another period. Using the next period can be undesirable, because it lowers the throughput of the entire system. In some embodiments, repeating steps 200 during the next period can usurp that entire period, which may be much longer than is typically allocated to mixing method 200. Accordingly, executing steps 200 during more than one period may result in relatively large amounts of down time in ACA 10. Accordingly, it is desirable to allocate enough of a period to mixing method 200 to allow for a number of cycles sufficient to pass a large fraction of samples at steps 220 and 230. In some embodiments, 8 cycles of method 200 can achieve over 95% successfully mixed and tested samples. This causes method 200 to utilize a substantial fraction (such as 50% or more) of a period.

At step 222, if additional time is available for further iterations of the cycle 200, the probe tip moves back to position A at step 204a to dispense at step 206 the aspirated portion of sample taken at position B. Like step 216, the dispensing process at step 206 aids in volume transfer between the different layers in the sample and can be monitored using transducer 78 and determine pressure values to be used in further calculations of delta. Cycle 200 then repeats until the sample meets acceptable homogeneity or the sample is rejected. It will be appreciated that this method may be suitable for other types of colloidal samples other than whole blood, as well. It should be noted that in some embodiments, there may be deviation between the location of the dispense at step 206 and the aspiration 208, as both can occur approximately at position A, perhaps deviating by a few mm.

In some embodiments, the final aspiration of the sample occurs near the middle height of the sample. This assists in achieving a sample that is most representative of a completely homogenized sample. Pressures experienced at the third location by the pressure transducer can be observed and used to determine the pressure slope during aspiration or dispensing at this third location. This third pressure slope can be compared to the pressure slopes at positions A or B to determine if the sample is suitably mixed. For example, a new delta can be calculated and compared to a threshold as described above.

If a probe is equipped with horizontal drive mechanisms sufficient to mechanically stir/mix a sample, in addition to mixing by aspiration/dispensing, the mechanical stirring can be used to enhance the re-suspension of sample components. A single mix-aspirate-dispense cycle may be sufficient to re-suspend the sample just prior to aspirating and dispensing a small portion of the sample for transfer to another vessel for the next step in an assay. Here, the stirring motion can be the primary mixing method and the aspiration/dispensing action can be used to verify the homogeneity of the sample. By using a mixing step (whether by stirring or one or more cycles of sip-and-spit), the time between mixing and aspiration can be consistent and near zero. The next step in an assay of the colloidal sample can begin with the assumption that each sample is homogeneous, much like handling non-colloidal solutions.

Some embodiments of the present invention can be implemented on existing architectures of both the system and front end automation without any fundamental changes. Using a sip-and-spit motion to re-suspend components of a colloid, such as whole blood, and to monitor the homogeneity of a sample allows handling of these samples on existing hardware with a software update. This is useful because the life cycle of an ACA can be several years. Enabling more automated handling of whole blood can give operators access to more assays as they become available, without requiring expensive upgrades. Another advantage of implementing embodiments of the present invention via software updates is that configuration can allow a user to enable or disable the feature. If the user prefers to use a manual nutation and a Stat approach to the sample, the user can be given this option. This allows a single ACA that can be enabled for colloidal/whole blood handling in accordance with the methods described herein, or the ACA can be configured without this feature. This allows options for users and can enable differing cost structures.

For example, some embodiments can be implemented with a software update to an ACA, such as the classic Dimension® clinical chemistry analyzer sold by Siemens Healthcare Diagnostics Inc. of Deerfield, Ill. In an exemplary machine, sample aspiration probe 54 has an ultrasonic mixer to re-suspend the sample in small secondary containers (in aliquot plates 44) just prior to aspiration. In an exemplary machine, the sampling probe 42 on this system, which is used to transfer a small amount of the sample onboard the system, may not contain a mechanical mixer. Sampling probe 42 is typically used to simply transfer an aliquot of the primary sample 40 into a small well in plate 44 to be used by sample probes on the system to run tests. However, instead of just taking a single aspiration from vessel 40 and dispensing it into a well, sampling probe 42 can be used to mix the sample by conducting one or more aspirations and dispenses (sip-and-spit). This method can also be used by reagent aspiration probe 60 for colloidal reagents that settle out and need to be thoroughly mixed.

Utilizing the methods of the present invention, it can be possible to utilize whole blood samples for assays without concern of how long a whole sample sits at any portion of the handling system. This allows a host of whole-blood tests to be performed as routinely as any other assay. These tests may include HbA1c (measuring the ratio of hemoglobin A1c, glycated hemoglobin in erythrocytes), ethanol, glucose, red blood cell folate (RBCFOL), immunosuppressive drug (ISD) tests, such as cyclosporine (CSA), tacrolimus (TACR), and sirolimus (SIRO), and various hemoglobin assays. Some embodiments are suitable for use with any of these whole blood assays.

CSA, for instance, is sensitive to heterogeneous samples. Sampling from the top or the bottom of the partially separated sample will produce CSA results that differ essentially linearly with respect to the red cell concentration. Therefore, a seemingly small 10% change in the red cell concentration from as little as 10 minutes of settling can cause a 10% shift in the analytical test result. This naturally led to studies to determine how long the sample could settle at each stage in the sample handling process without changing the result by more than 5%. Different patient samples settle at different rates and those with fewer red cells and less viscous blood can settle very quickly. In the prior art it was common for a maximum allowable settling time for a 200 uL sample aliquot of whole blood to be <10 minutes. Another challenge is the fact that CSA uses lyophilized tablets for its reagents that require hydration prior to use. If there are no reagent wells pre-hydrated for CSA, it will take >10 minutes to hydrate, mix, and QC a set of reagents to run a CSA test. Therefore, if the sample expiration was set to 10 minutes; often the sample would expire before the reagents were ready for the test to begin.

By utilizing the methods discussed herein, the timing of assays, such as CSA, can be handled automatically, without concern by the operator. For example, using a random access approach to sample handling, a whole blood sample can be inserted into the machine on input lane 35 and the analyzer 10 can begin preparing reagents upon reading the barcode on sample tube 40. Whereas prior art system could suffer assay errors by allowing whole blood samples to sit, embodiments of the present invention can be used to ensure that sample is re-suspended/homogenized at the time of each transfer. Accordingly, using random access, the analyzer 10 can handle the whole blood sample on a schedule convenient to operation of the entire system, rather than declaring every whole blood sample a Stat sample for immediate handling. This is particularly desirable when operating an ACA with high-volume throughput, such as performing several hundred assays per hour, likely on hundreds of input samples.

Accordingly, the potential benefits of using embodiments of the present invention may include: processing whole blood samples among all other sample types without any special restrictions or sample limits; not restricting the number of whole blood samples beyond the space available on the system for placing sample racks; allowing whole blood tubes on the same sample rack (they can be mixed with other fluid types on any rack) as other samples, and eliminating or reducing the pre-processing steps involved. Because a whole blood sample (or other colloidal sample) can be identified via its barcode (or other indicia), many embodiments effectively allow an operator to disregard sample type when placing the samples on the instrument.

It should be noted that whole blood samples may still need to be handled according to best-practices whole blood handling instructions, such as avoiding centrifugation and mixing the sample by hand right after taking it from the patient (to dissolve the anti-coagulant in the sample). Also, the sample shall not be left uncapped to evaporate for longer than a serum or plasma tube would be left uncapped.

Some embodiments may be capable of re-suspending a whole blood sample that has settled by sitting upright at 25° C. for up to 4 hours with the aliquot probe in 43.2 seconds including all washing steps. The re-suspended whole blood sample's Hemoglobin (Hb) concentration may then be within 5% of a freshly mixed sample from the same patient. Embodiments may also be able to detect failure to re-suspend a sample. Failure can be caused by many things, including using a sample that has settled for more than 4 hours, mishandling such as freezing samples, using very old samples, or failing to utilize an anti-coagulant agent. In the event of an aberrant sample, the system may generate an error and/or retry to mix a heavily settled sample. In some embodiments, if the system detects the wrong sample type or a dangerously viscous sample, it may not retry and will flag a separate error.

One challenge in using the methods discussed herein with existing systems that include multiple sample types other than whole blood is cross contamination and cleaning. A whole blood sample may be used in an ACA that also handles other sensitive assays. For example, the same probe is used to aspirate samples for assays like BhCG (pregnancy test); where the carryover requirement is less than 1 ppm. The nature of mixing with aspiration and dispense can create lots of potential carryover by coating the inside and outside of the probe with the whole blood sample. Therefore, the probe should be extensively washed and cleaned between each sample. During operation of a typical aliquot sequence, the probe goes into bleach and aspirates the bleach right at the beginning of a sequence to clean off any carryover from the previous sample. Then, the probe must be rinsed with enough water to reduce the bleach carryover into the next sample; and then the probe must be dried to prevent water carryover into the next sample. This approach works well for serum/plasma and urine samples that do not react with bleach and form a precipitate. Whole blood, however, may react with bleach and form small black tar-like balls that could clog the probe or the drain. This can greatly reduce the service life of a probe needle and reduce accuracy.

Figure 9:
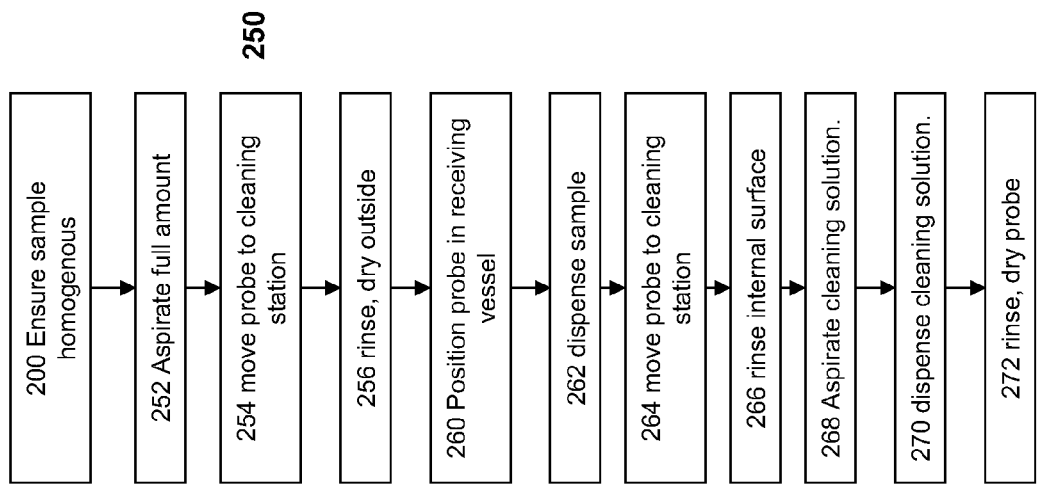
FIG. 9 is a flow diagram of the operation of a post-mixing procedure for use with certain embodiments.

FIG. 9 presents a method that describes an exemplary cleaning routine 250 that addresses the issues experienced when handling hazardous samples that may react with bleach. Routine 250 begins after a sample, such as whole blood, has been interacted with by the probe needle. An example of this interaction is described in FIG. 8, routine 200, which verifies that the whole blood sample is homogenized. After interaction, at step 252, the probe aspirates a sample. This can be a similar, smaller, or larger quantity than the amount used during the sip-and-spit process and need not be substantially the entire sample in a vessel. This is the amount of sample, such as 200 uL, being transferred to another vessel, such as a reaction vessel to perform the next assay task.

At step 254, the ACA moves the probe needle to a cleaning station. This station includes a drain and water sprayer. At step 256, to mitigate cross contamination, the probe dives into the drain and is showered with water or non-reactive solution. This step can include partially submerging the probe needle on a water bath, as well. Furthermore, this reduces the amount of sample that may be dripped or otherwise cross contaminate other assays or samples as the probe is moved into place at the destination vessel. This also assists in preventing reaction with any subsequent bleach cleaning steps, as most or all blood will be removed by the water spray. The sample stored in the vessel remains undisturbed. Following the rise, the needle is dried, such as via a fan or air knife. This reduces the chance of dripping water as the probe travels and reduces overall carryover between vessels.

At step 260, the ACA positions the probe to interact with a destination vessel. This is the vessel, such as a reaction vessel or an aliquot well, into which the stored sample will be dispensed. At step 262, the probe dispenses the sample into the destination vessel. It may then interact with the sample, as well, such as performing a mixing action on the resulting solution. Once the probe is empty of a sample, it is ready to be fully cleaned.

At step 264, the probe moves to the cleaning station, which may be the same or another station from step 254. Whole blood and bleach should not be mixed and some embodiments use bleach for eliminating carryover between one sample aspiration and the next. Accordingly, it is desirable to rinse the probe thoroughly before entering bleach or other cleaning solution. Rinsing the probe, step 266, inside and out after mixing is helpful because this is a sequence that is random access, and the next sample may be very sensitive to carryover. The interior of the probe is purged with water after the sample is dispensed to reduce the whole blood remaining on the probe to desirably less than 1000 ppm. To accomplish this, the probe rinses its internal surface with water, such as via wash manifold 60M in FIG. 4, flushing the surface with a quantity of water. In addition, the outside of the probe needle may be rinsed with an external sprayer and/or water bath at the cleaning station, to further reduce sample outside the needle. This water falls into a drain at the cleaning station.

In some embodiments, after the probe leaves the rinsing well, the well and drain are themselves purged and rinsed to ensure that the well remains clean for the next interaction with the probe.

At step 268 the probe is dipped into a cleaning solution, such as bleach, and aspirates the solution. Because the probe was rinsed at step 266, any reaction between the cleaning solution and sample residue will be minimized. At step 270, the cleaning solution is dispensed, leaving a cleaned internal and external surface of the probe needle. To reduce cleaning solution residue, the outside of the probe needle is again rinsed via a water spray at step 272 and the internal surface of the probe needle is flushed with water via the wash manifold. The probe is then briefly dried via a fan or air knife, resulting in a clean dry probe.

It will be appreciated that the timing of these steps of method 250 can be coordinated with the timing of the motion of samples on a sample input conveyor or other motion, such as the rotation of the carousel 12. For example, the steps before step 256 can occur before the motion, while subsequent steps occur after the motion. Furthermore, the steps can be timed to take less than one motion step to complete to minimize down time and, in some embodiments, the cleaning steps are completed in sufficient time to allow the probe needle to perform an aspiration and/or mixing task before the operational period expires. This allows cleaning to occur once per motion step or operational period in the system.

In some embodiments, the overall period available for a sample aspirate and dispense sequence is around 40 seconds. This time must be judiciously used, as this provides a cycle time for the components of the system. Steps and methods that cannot be completed in a single period must spend another period to complete, greatly reducing overall throughput of the system. In some embodiments, the sip-and-spit method described in FIG. 8 will complete in a fraction of a period such as 2 seconds, as the probe participates in other steps, such as moving, cleaning, and fluid transfer. In some embodiments, the time used can be reduced by moving the probe tip 42T while performing dispense steps 216 and 206; in other embodiments the tip is held steady during dispense steps. In some embodiments, the pump and the probe are controlled by separate microprocessors and by executing commands sequentially; the pump will wait for the probe to finish and vice versa.

In addition, the time taken to aspirate and dispense during the routine described in FIG. 8 can vary. For example, top dispenses may be at a slower speed if the probe is out of the fluid when the aspiration begins and is submersed towards the end of the dispense. This means that higher speed aspirations can cause foaming. Also, because the probe is not deeply in the fluid, there may not be much advantage to a higher speed dispense for mixing action. In this case, the top dispense remains useful for volume transfer of hematocytes from the bottom of the sample to the top.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed:

1. A method of mixing a sample by an analyzer comprising the steps of:
    (a) aspirating a first portion of a sample to be mixed from a first level within a vessel containing the sample;
    (b) dispensing the first portion of the sample at a second level within the vessel;
    (c) measuring a first set of one or more pressure values using a sensor coupled to a pipette during at least one of the steps of aspirating or dispensing the first portion of the sample;
    (d) aspirating a second portion of the sample to be mixed from approximately the second level within the vessel;
    (e) dispensing the second portion of the sample at approximately the first level within the vessel;
    (f) measuring a second set of one or more pressure values using the sensor during at least one of the steps of aspirating or dispensing the second portion of the sample;
    (g) comparing the first and second set of values to determine a difference of the one or more pressure values of the first and second samples, wherein the difference indicates a level of relative homogeneity between the first and second portions of the sample;
    (h) determining by the analyzer whether the level of relative homogeneity between the first and second portions meets predetermined criteria; and
    (i) transferring at least a third portion of the sample to perform an assay if the determining step indicates that the sample is sufficiently mixed.

2. The method of claim 1, wherein the sample is whole blood.

3. The method of claim 1, wherein the sample is a fluid having components that separate over time.

4. The method of claim 1, wherein the first level is a location substantially near the top surface of the sample.

5. The method of claim 1, wherein the first level is a location substantially near the bottom of the sample.

6. The method of claim 1, wherein one of the first level and second level is a location substantially near the top surface of the sample and the other of the first level and second level is a location substantially near the bottom of the sample.

7. The method of claim 1, wherein the steps of aspirating and dispensing are repeated a predetermined number of times, such that multiple first portions of the sample are transferred from the first level to the second level and multiple second portions of the sample are transferred from the second level to the first level.

8. The method of claim 1, wherein the steps of aspirating and dispensing are repeated, such that the multiple first portions of the sample are transferred from the first level to the second level and multiple second portions of the sample are transferred from the second level to the first level, until the difference of the at least one property of the first and second samples meets predetermined criteria.

9. The method of claim 8, further comprising rejecting the sample if the sample fails to meet the predetermined criteria after a predetermined number of times.

10. The method of claim 1, wherein the predetermined criteria includes an indication that the viscosities of the first sample portion and second sample portion are substantially similar.

11. The method of claim 1, wherein the first set and second set of one or more values comprise a first set and second set of one or more pressure values comprising a slope.

12. The method of claim 11 further comprising:
calculating a first pressure drop from the first set of one or more pressure values and a second pressure drop from the second set of one or more pressure values; and
wherein the determining step includes determining whether the first and second pressure drops meet a threshold of similarity.

* * * * *